United States Patent
Lindner et al.

(10) Patent No.: US 8,491,663 B2
(45) Date of Patent: Jul. 23, 2013

(54) PROSTHESIS FOR PART OF A JOINT, WITH AN ANTI-TWIST ELEMENT

(75) Inventors: Nicola Lindner, Wurmlingen (DE); Stephan Eckhof, Rietheim-Weilheim (DE); Thomas Feldhaus, Tuttlingen (DE)

(73) Assignee: Zrinski AG, Wurmlingen (DE)

( * ) Notice: Subject to any disclaimer, the term of this patent is extended or adjusted under 35 U.S.C. 154(b) by 0 days.

(21) Appl. No.: 12/452,555

(22) PCT Filed: May 9, 2008

(86) PCT No.: PCT/IB2008/001243
§ 371 (c)(1), (2), (4) Date: Jan. 8, 2010

(87) PCT Pub. No.: WO2009/007805
PCT Pub. Date: Jan. 15, 2009

(65) Prior Publication Data
US 2010/0137994 A1    Jun. 3, 2010

(30) Foreign Application Priority Data

Jul. 9, 2007 (DE) .................... 20 2007 009 620 U

(51) Int. Cl.
*A61F 2/42* (2006.01)
(52) U.S. Cl.
USPC .............. 623/21.15; 623/21.11; 623/23.44; 623/23.45
(58) Field of Classification Search
USPC .............. 623/21.11, 21.15, 23.44, 23.45
See application file for complete search history.

(56) References Cited

U.S. PATENT DOCUMENTS

| | | | | | |
|---|---|---|---|---|---|
| 3,805,302 | A | * | 4/1974 | Mathys | 623/21.15 |
| 4,011,603 | A | * | 3/1977 | Steffee | 623/21.16 |
| 4,059,854 | A | * | 11/1977 | Laure | 623/21.16 |
| 4,242,759 | A | * | 1/1981 | White | 623/21.15 |
| 4,304,011 | A | * | 12/1981 | Whelan, III | 623/21.16 |
| 4,352,212 | A | | 10/1982 | Greene et al. | |
| 4,624,673 | A | * | 11/1986 | Meyer | 433/173 |
| 5,147,386 | A | * | 9/1992 | Carignan et al. | 623/21.16 |
| 5,370,695 | A | * | 12/1994 | Meuli et al. | 623/23.53 |

(Continued)

FOREIGN PATENT DOCUMENTS

| | | |
|---|---|---|
| DE | 23 38 136 | 1/1975 |
| DE | 295 14 169 | 11/1995 |

(Continued)

OTHER PUBLICATIONS

International Search Report.

*Primary Examiner* — Thomas J Sweet
*Assistant Examiner* — Seema Mathew
(74) *Attorney, Agent, or Firm* — Collard & Roe, P.C.

(57) ABSTRACT

The invention relates to a joint part prosthesis, particularly for a finger joint, consisting of either a proximal or a distal component, as well as a shaft that extends away from this component, to be mounted in a bone, which shaft is configured with a fin-like anti-twist device. According to the invention, it is provided that as an anti-twist device (7), at least two anti-twist elements (8) are disposed on the mantle surface (6) of the shaft (4), with rotation symmetry, and extend radially away from this mantle surface (6) and in the longitudinal direction of the shaft (4), whereby the distance of the anti-twist elements (8) from the mantle surface (6) decreases slightly in the direction toward the free end (5) of the shaft (4).

2 Claims, 2 Drawing Sheets

U.S. PATENT DOCUMENTS

Figure 1:
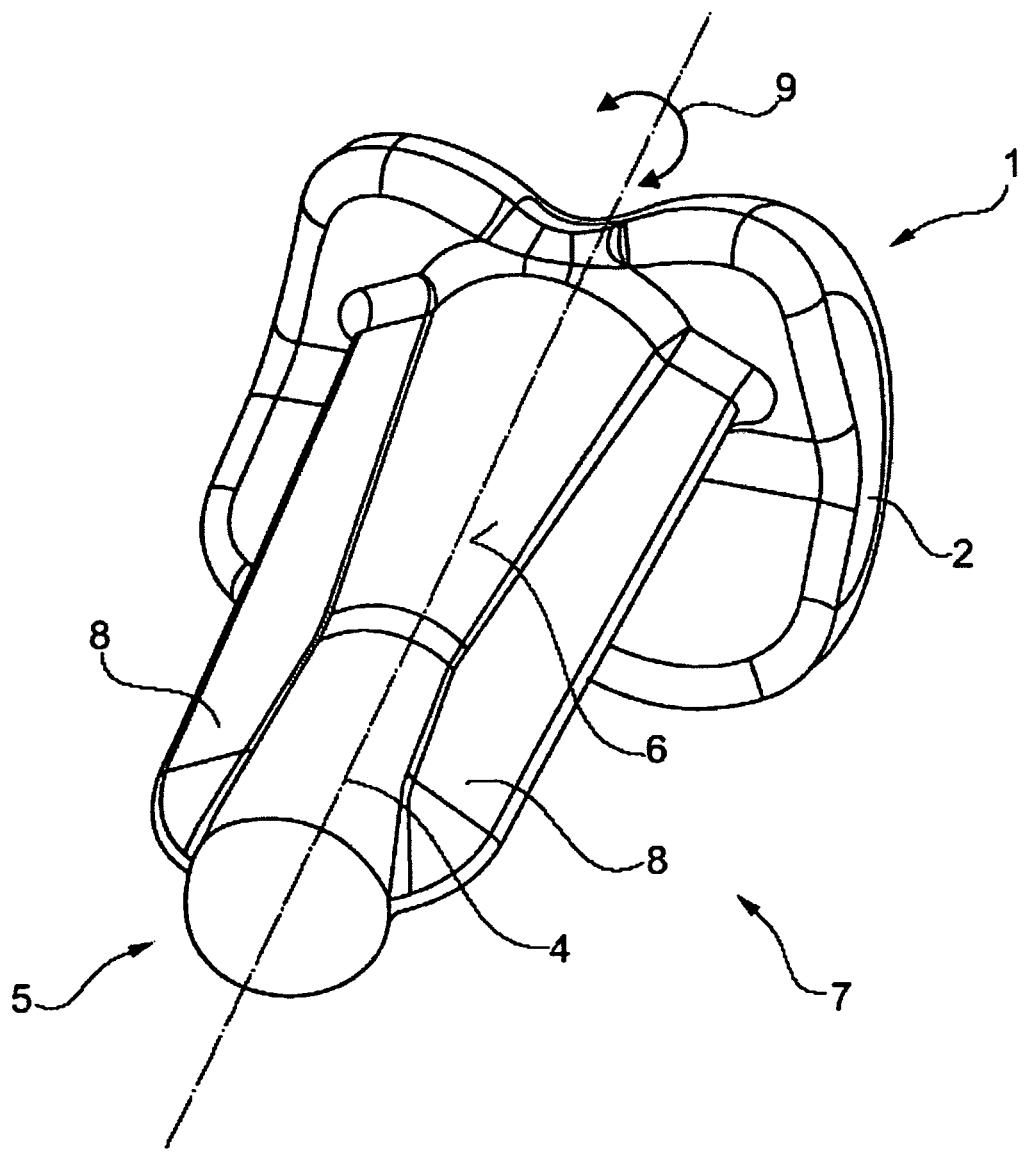

| | | | |
|---|---|---|---|
| 5,413,609 A * | 5/1995 | Nicol et al. | 623/21.15 |
| 5,674,297 A * | 10/1997 | Lane et al. | 623/21.16 |
| 6,251,141 B1 | 6/2001 | Pierson, III et al. | |
| 6,342,076 B1 * | 1/2002 | Lundborg | 623/21.15 |
| 6,352,560 B1 * | 3/2002 | Poeschmann et al. | 623/23.4 |
| 2001/0025199 A1 | 9/2001 | Rauscher | |
| 2003/0004576 A1 | 1/2003 | Thalgott | |
| 2003/0040805 A1 * | 2/2003 | Minamikawa | 623/23.46 |
| 2004/0236431 A1 * | 11/2004 | Sekel | 623/23.44 |
| 2006/0030945 A1 * | 2/2006 | Wright | 623/20.15 |
| 2008/0109081 A1 | 5/2008 | Bao et al. | |
| 2011/0004255 A1 * | 1/2011 | Weiner et al. | 606/301 |

FOREIGN PATENT DOCUMENTS

| | | |
|---|---|---|
| DE | 101 30 796 | 1/2003 |
| EP | 1 203 569 | 5/2002 |
| FR | 2 653 660 | 5/1991 |
| WO | WO 03/065939 | 8/2003 |
| WO | WO 03/099171 | 12/2003 |
| WO | WO 2005/030087 | 4/2005 |
| WO | WO 2006/074414 | 7/2006 |

* cited by examiner

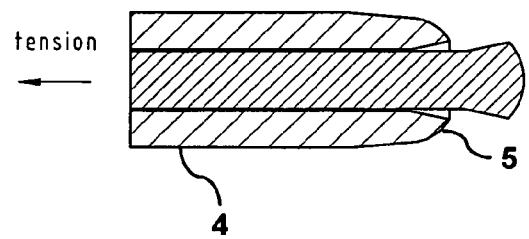
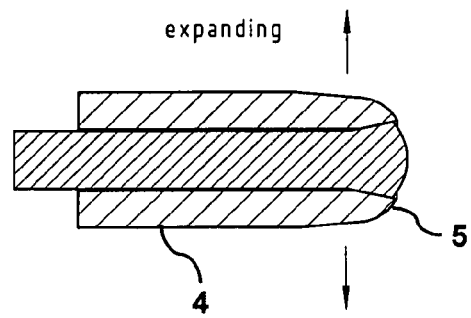
FIG. 2　　　　　　　　　　　　FIG. 3
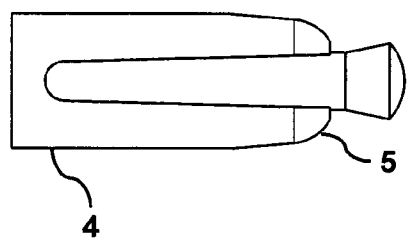
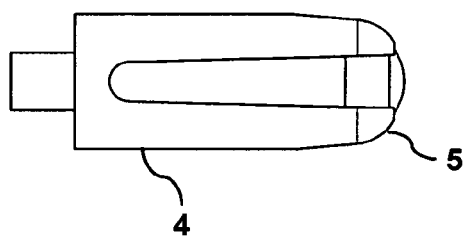
FIG. 4　　　　　　　　　　　　FIG. 5
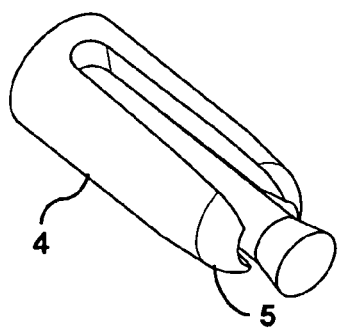
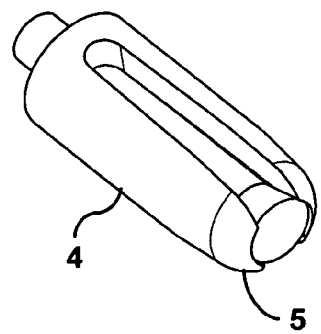
FIG. 6　　　　　　　　　　　　FIG. 7

PROSTHESIS FOR PART OF A JOINT, WITH AN ANTI-TWIST ELEMENT

CROSS REFERENCE TO RELATED APPLICATIONS

This application is the National Stage of PCT/IB2008/001243 filed on May 9, 2008, which claims priority under 35 U.S.C. §119 of German Application No. 20 2007 009 620.8 filed on Jul. 9, 2007. The international application under PCT article 21(2) was not published in English.

TECHNICAL FIELD

The invention relates to a joint part prosthesis, particularly for a finger joint. It consists of either a proximal or a distal component, as well as a shaft that extends away from this component, to be mounted in a bone, the shaft having a fin-like anti-twist safety element.

STATE OF THE ART

Artificial finger joints consist essentially of two elements, namely a proximal and a distal component. A component has a convex joint head that interacts with the other part, which demonstrates a convex joint socket.

Artificial finger joints are inserted between the metacarpal bone and the finger bone, or between individual finger bones. Such joints have to be inserted if degenerative joint diseases such as osteoarthritis, post-traumatic arthritis, or rheumatoid arthritis of the joints in question are present. Another alternative that retains mobility of the individual finger members is a total joint replacement.

From the state of the art, particularly from EP 1203569 A (FINSBURY (DEVELOPMENT) LIMITED LEATHERHEAD) Mar. 3, 2000, finger joint implants are known in the configuration of so-called PIP shaft implants. They have a proximal or a distal component, which components interact accordingly, each having a shaft that points away from these components. The shaft is generally configured to be conical and is introduced into the bone marrow of a bone. In order to allow introduction, the interior of the bone is partly cleared out using a clearing tool, and the implant is driven into the bone using a hammer-like instrument. Fixation takes place in such a manner that the diameter of the cleared bore is smaller than the outside diameter of the shaft, so that a kind of press fit is formed between the shaft and the interior of the bone.

The implant itself consists of a material having a modulus of elasticity similar to bone. This modulus of elasticity similar to bone avoids so-called stress shielding and thus promotes bone build-up. Additionally, fixation of the implant in the medullary space of the bone is improved in this manner.

Furthermore, a joint part prosthesis is known from DE 101 30 796 Al (MUENDER ULRICH [DE]) 23.01.2003, which is particularly supposed to be used for diseased finger joints. Here, the artificial joint possesses so-called implant stems for its attachment to the adjacent bone, which stems have stabilization wings that run out very conically in their initial regions, to improve their rotation stability. Preferably, four stabilization wings are provided, in each instance, which are not only supposed to improve the production process when using a wax injection-molding technique, but also to take over the task of joint body stabilization against possible shrinkage or a change in geometrical shape.

DISADVANTAGES OF THE STATE OF THE ART

Products according to the state of the art have disadvantages such as implant loosening due to insufficient fixation and insufficient connection with the bone, as well as high wear values, thereby causing corresponding friction wear. The shaft-like construction within the medullary space creates sufficient room for itself if loosened, so that an implant that was fixed in place previously is no longer functionally correct. The consequences of this are pain caused by migration or even fractures.

Furthermore, the disadvantage of the embodiments according to the state of the art consists in that the individual joint part prostheses cannot be disposed in a manner to reliably prevent twisting.

TASK OF THE INVENTION

It is therefore the task of the invention to further develop a joint part prosthesis, particularly for finger joints, in such a manner that the likelihood of loosening of the implant is reduced, in contrast to the state of the art, and, at the same time, insertion of the prosthesis is simplified.

SOLUTION OF THE TASK

The core idea of the solution of the task is that at least two wing-like or fin-like anti-twist elements are disposed on the mantle surface of the shaft to be mounted in a bone, with rotation symmetry, and extend radially from the mantle surface and in the longitudinal direction, whereby the distance of the anti-twist elements from the mantle surface decreases slightly in the direction of the free end of the shaft.

ADVANTAGES OF THE INVENTION

One of the significant advantages of the invention is that because of the configuration of the joint part prosthesis according to the invention, it is no longer necessary to clear out the medullary space of the bone into which the implant is to be placed by means of working on it by hitting or hammering. Nevertheless, the joint part prosthesis can be fixed in place in simple and efficient manner. Since the shaft of the joint part prosthesis has rotation symmetry, it is sufficient to clear out the medullary space of the bone by means of rotational movements. In this way, damage to adjacent joints, in particular, caused by the hammering process required for clearing, is avoided.

One of the other significant advantages of the invention is that the joint part prosthesis can be inserted into the medullary space of a bone, with its shaft, and is also fixed in place there, in anti-twist manner, without additional steps being required.

The anti-twist device provided on the mantle surface of the shaft of the joint part prosthesis, according to the invention, which device comprises at least two fin-like elements, advantageously extends in a longitudinal expanse of the shaft. In this connection, the fin-like elements are preferably narrow, and advantageously configured to be somewhat thicker toward the shaft. This brings with it the advantage that for one thing, torques/torsions that occur can be absorbed by the anti-twist element. For another thing, it has the advantage, because of the fact that the free ends are configured to be narrower, that simple insertion into the prepared cleared medullary space is possible.

A preferred embodiment of this anti-twist security device provides that it/they increase in their reaches, proceeding from the free end, in the direction of the distal or proximal component, so that twisting is still possible at insertion of the implant, and the farther the implant is introduced into the medullary space, the more likely it is that twisting is configured to be restricted.

In order to be able to install such anti-twist devices together with the shaft of a component, it is provided to clear the cavity accordingly. Aside from the dimensions of the shaft, the spaces that project away laterally are also cleared by means of a gauge, so that the implant can be inserted with precise fit. Clearing preferably takes place by means of rotating and oscillating movements, so that no hammering movements, which put stress on the joints, are required.

In one exemplary embodiment, the joint part prosthesis consists of a material that is known from the state of the art.

Preferably, the anti-twist elements form a one-piece part with the shaft.

A preferred embodiment provides that the distance from the mantle surface of the shaft decreases toward the free end of the anti-twist element, in the direction of the free end of the shaft.

Furthermore, it is provided that a plastic can be used, particularly in order to achieve the modulus of elasticity similar to bone. This also brings with it the particular advantage that the joint part prostheses can be produced by means of injection-molding methods.

Other advantageous embodiments are evident from the following description, the drawings, as well as the claims.

DRAWING

The drawings show:

FIG. 1 is a perspective view of the joint part prosthesis according to the invention, with a proximal component, with an anti-twist security device disposed on it, and FIGS. 2-7 are views of the joint part prosthesis of FIG. 1 with the anti-twist security device removed to illustrate the shaft having a narrowing towards the free end.

DESCRIPTION OF AN EXEMPLARY EMBODIMENT

In FIG. 1, an embodiment according to the invention is shown. The joint part prosthesis 1 shown there comprises a proximal component 2, from which a shaft 4 extends to the rear. The shaft 4 extends almost perpendicular away from the proximal component 2 and has a narrowing toward its free end 5 in the exemplary embodiment shown here. It is configured to be round in cross-section. The round cross-section brings with it the advantage that this embodiment can be produced in simpler and more cost-advantageous manner than an oval or rectangular shape, for example.

The free end 5 of the shaft 4 is preferably configured in ball-like manner, so that no sharp edges can be formed, which can injure any marrow of the bone during insertion of the prosthesis.

Furthermore, the wall of the shaft 4 is configured to be round, particularly in the region of the free end 5.

On the mantle surface 6, the anti-twist device 7 according to the invention is disposed. This anti-twist device 7 serves to fix a shaft 4, that has been introduced into a medullary space, in place in such a manner that turning of the joint part prosthesis 1 within the medullary space is no longer possible, whereby the medullary preferably has a cross section, which at least almost corresponds to a cross-section of the shaft 4 with its anti-twist device 7.

The anti-twist device 7 consists of at least two anti-twist elements 8 which expand in the longitudinal extension of the shaft 4 and have a fin-like construction.

Particularly in the region of the free end 5 of the shaft 4, it is provided to configure the anti-twist elements 8 very slightly, with regard to their distances from the mantle surface of the shaft 4, so that during introduction, corresponding positioning within the medullary space is still possible. The deeper the joint part prosthesis 1 is introduced into the medullary space, the more the fin-like anti-twist elements 8 penetrate into the medullary space and press themselves into the marrow of the bone. A corresponding wedge effect occurs.

The anti-twist elements 8 prevent a rotational movement of the joint part prosthesis 1 in or opposite to the arrow direction 9. They serve as a fixation of the joint part prosthesis 1 in the rotation direction, but also in the longitudinal direction.

The invention can be used for joint part prostheses in both the distal or the proximal region. Likewise, use for all types of prostheses that have a shaft-like configuration is possible, where it is important to prevent a rotational movement of the joint part prostheses from being possible.

REFERENCE SYMBOL LIST 1 joint part prosthesis
2 proximal component
3 -
4 shaft
5 free end
6 mantle surface
7 anti-twist device
8 anti-twist element
9 arrow direction

The invention claimed is:

1. A joint part prosthesis comprising:
(a) a proximal or distal component;
(b) a shaft to be mounted in a bone, said shaft having a longitudinal axis extending away from the proximal or distal component and comprising a free end and a mantle surface, the shaft being configured to be round in cross-section to have an outer diameter in the cross-section and being configured to be spherical at the free end, the outer diameter of the cross-section being smaller in a mid-region of the shaft than at both the free end of the shaft and at an end of the shaft adjacent the proximal or distal component, the outer diameter continually increasing from said mid-region to said free end of the shaft and from said mid-region to said end of the shaft adjacent the proximal or distal component; and
(c) a fin-like anti-twist device comprising at least two fin-like anti-twist elements disposed on the mantle surface with rotational symmetry and extending radially from said mantle surface in a longitudinal direction of the shaft to a radial distance from the mantle surface, the radial distance decreasing slightly in a direction toward the free end of the shaft, the at least two fin-like anti-twist elements starting at the free end of the shaft;
wherein the at least two fin-like anti-twist elements have a first thickness at a first location toward a free lateral side of the fin-like anti-twist elements and a second thickness at a second location toward the shaft, the first location being disposed along a first line perpendicular to the longitudinal axis of the shaft, the second location being disposed along the same first line perpendicular to the longitudinal axis of the shaft, and the second thickness being greater than the first thickness; and
wherein during insertion of the shaft into a medullary space of a bone, rotational movements of the shaft clear the medullary space and the at least two fin-like anti-twist elements fix the joint part prosthesis in place in the medullary space so as to prevent rotation.

2. The joint part prosthesis according to claim 1, wherein said prosthesis is produced in one piece, as a plastic injection-molded part.

* * * * *